(12) United States Patent
Dungworth

(10) Patent No.: US 6,407,161 B1
(45) Date of Patent: Jun. 18, 2002

(54) POLYMERIZATION PROCESSES AND PRODUCTS AND USES OF THE PRODUCTS

(75) Inventor: Howard Roger Dungworth, Norland (GB)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/508,149

(22) PCT Filed: Sep. 11, 1998

(86) PCT No.: PCT/GB98/02748

§ 371 (c)(1),
(2), (4) Date: Mar. 7, 2000

(87) PCT Pub. No.: WO99/14246

PCT Pub. Date: Mar. 25, 1999

(30) Foreign Application Priority Data

Sep. 12, 1997 (GB) .............................................. 9719473

(51) Int. Cl.[7] .............................. C08F 2/32; C08L 33/06; C08K 7/16
(52) U.S. Cl. ........................ 524/801; 524/555; 524/916; 523/105; 523/223; 523/342
(58) Field of Search ................................ 524/555, 801, 524/916; 523/223, 342, 105

(56) References Cited

U.S. PATENT DOCUMENTS

| 2,625,529 | A | * | 1/1953 | Hendrick et al. |
| 3,892,702 | A | * | 7/1975 | Burke, Jr. |
| 5,744,520 | A | * | 4/1998 | Kmiecik-Lawrynowicz et al. |
| 5,912,294 | A | * | 6/1999 | Schade |

FOREIGN PATENT DOCUMENTS

| EP | 0214758 | 3/1987 |
| FR | 2254583 | 7/1975 |
| GB | 1493356 | 11/1977 |

OTHER PUBLICATIONS

Ullmann's Encyclopedia of Industrial Chemistry, 5th Edition, vol. A16 (1990), p. 442.

* cited by examiner

*Primary Examiner*—Tae H. Yoon
(74) *Attorney, Agent, or Firm*—Kevin T. Mansfield

(57) ABSTRACT

Dry particulate polymeric products, generally spray dried granules, are made by reverse phase polymerization in a partially water miscible continuous phase in the presence of an ionizable stabilizer which is water soluble when ionized and water insoluble when unionized, with the result that all the contamination in the products can be water soluble or miscible. The products are of value as flocculants and viscosifiers, for instance for cosmetic or pharmaceutical clear gels.

20 Claims, No Drawings

POLYMERIZATION PROCESSES AND PRODUCTS AND USES OF THE PRODUCTS

This invention relates to polymers made from water soluble ethylenically unsaturated monomer or monomer blend, and in particular to dry granular polymers and their uses.

There are various ways of making such polymers including, for instance, precipitation polymerisation, bulk gel polymerisation and reverse phase polymerisation. Precipitation polymerisation has the disadvantage that the molecular weight of the polymers (if made in the absence of cross linker) tends to be rather low (for instance not more than intrinsic viscosity 1 dl/g) with the result that cross linked polymers made by this technique have an undesirably short chain length between adjacent cross links.

Bulk gel polymerisation is a convenient technique but it involves comminution and gives a wide spread of particle sizes.

Reverse phase polymerisation has the advantage that it can give a more uniform particle size. Unfortunately the products are always contaminated with hydrophobic materials.

Reverse phase polymerisation processes comprise providing a dispersion of droplets of an aqueous monomer phase dispersed in a continuous phase in which is dissolved a polymeric stabiliser for the droplets, and polymerising the monomer in the droplets to produce a dispersion of aqueous polymer droplets in the continuous phase.

When the droplets are large (typically above 100 $\mu$m) this is a bead polymerisation process and the aqueous polymer droplets are dried and separated from the dispersion as substantially individual dry beads.

When the aqueous monomer phase droplets are emulsified into the continuous phase the product is a substantially stable emulsion of the aqueous polymer droplets (having a size substantially all below 10 $\mu$m and often below 3 $\mu$m) in the continuous phase. The emulsion can be subjected to dehydration so that the droplets which are dispersed in the continuous phase are substantially dry.

If the emulsion (with or without dehydration) is used as such, its use necessarily carries the continuous phase with the polymer into the environment where the polymer is being used.

It is known to recover dry polymer droplets as a powder from the continuous phase of the emulsion. For instance spray drying is mentioned in GB-A-905,779 and U.S. Pat. No. 4,035,317 and will lead to granular aggregates above 10 $\mu$m in size formed of the primary polymer particles which are below 10 $\mu$m in size.

Irrespective of whether the dry polymer is recovered as large beads or as granular aggregates, the polymer is always contaminated by contaminants from the production process. In practice, the polymeric stabiliser is always insoluble in water, irrespective of the pH of the water, and is typically a copolymer of, for instance, a relatively large amount of stearyl methacrylate together with some methacrylic acid. This stabiliser will have concentrated at the interface of the aqueous monomer droplets and the continuous phase, and thus the polymer beads or granules are always contaminated by significant amounts of it. Also the continuous phase is usually a hydrophobic liquid such as a hydrocarbon and residues of this are normally trapped in or on the granules or beads, and so cause further hydrophobic contamination. The granules made from the emulsions are usually further contaminated by water-in-oil, non-polymeric surfactant, such as sorbitan oleate, which is used to promote the emulsification of the aqueous monomer phase into the continuous oil phase.

These various hydrophobic and relatively water insoluble contaminants therefore tend to interfere with the performance of the granules or beads when they are mixed into water. For instance they tend to reduce the wettability of the granules or beads with water, which can be undesirable, and they tend to carry into the resultant aqueous composition contaminants which are unwanted and in some instances undesirable. For instance it can be undesirable deliberately to introduce surfactant into the aqueous composition, for instance when the polymer is to be used as a flocculant. It can be undesirable to include water immiscible components into the aqueous composition when the visual appearance of the resultant aqueous composition is important. For instance, in unpublished research we have established that aqueous gels made from such granules tend to be opaque because of the residual stabiliser and continuous phase and surfactant.

A known polymeric thickener for making clear aqueous gels for cosmetics and other purposes is a cross linked anionic polymer powder having a very small particle size made by precipitation polymerisation. Although a reasonably clear gel is obtained under pH conditions where the polymer is ionised, the polymer gives an inferior gel and inadequate performance at lower pH values, since the polymer is not then fully ionised. Since the pH of the human skin is around 5.5, it follows that these precipitated anionic polymers do not provide optimum clarity and performance in compositions which are convenient and suitable for application to the skin. Also the low molecular weight obtainable by precipitation polymerisation tends to detract from their performance.

In the invention, we now provide a novel reverse phase polymerisation process which can be conducted as a bead polymerisation process but is preferably conducted as an emulsion polymerisation process and we provide dry polymeric products obtainable from this process and which avoid the contamination which is conventionally associated with products made by reverse phase polymerisation.

According to the invention we provide a product comprising dry polymer particles which are substantially spherical and are formed of a polymer of water soluble ethylenically unsaturated monomer or monomer blend and which carry contamination by 2 to 30%, based on the dry weight of the polymer, of contaminants, wherein the contaminants are water miscible and include at least 2% (based on the dry weight of polymer) by weight of a stabiliser polymer containing ionisable groups whereby the stabiliser is soluble in water when substantially ionised but substantially insoluble in water when the ionisable groups are substantially non-ionised, and the contaminants are substantially free of materials which are not soluble in water at the pH at which the ionisable groups are substantially ionised.

The dry polymer particles can be polymer beads made by reverse phase bead polymerisation, in which event they normally have a size at least 90% above 50 $\mu$m, and generally below 1000 $\mu$m.

Preferably, however, the dry polymer particles are particles which have a size at least 90% by weight below 10 $\mu$m which are primary particles in dried granules which have a size at least 90% by weight above 10 $\mu$m and which are formed of the primary polymer particles and the contaminants. These dried granules are preferably made by spray drying the reverse phase emulsion but can be made by other techniques for recovering dry particles from such an emulsion, for instance precipitation and/or, preferably, film drying.

When the granules are to be used as viscosifiers, especially for cosmetics, the granules including the contaminants preferably provide a gel having a clarity of less than 25 NTU when mixed with deionised water to provide a composition containing 1% by weight of the granules and having a pH at which the ionisable groups are sufficiently ionised for the stabiliser to be soluble in that gel.

The invention also includes the clear gel made by mixing the granules with water and compositions (such as household and cosmetic, pharmaceutical or other personal care compositions) incorporating such a gel.

When the granules are to be used for other purposes, such as flocculants or other uses where they are to be dissolved into a large amount of water, the contaminants are preferably such that they do not deleteriously interfere with the dissolution of the granules into water to form the aqueous solution of flocculant, viscosifier, or other functional polymer.

Except where stated otherwise in this patent specification, solubility is judged in the context of the expected concentration of the polymeric material in the relevant solvent. Thus, by referring to the contaminants in the granules or beads as being soluble in water we mean that the contaminants will dissolve readily into water to give a clear solution at the concentrations which are likely to be encountered in practice when using the polymer. Typically therefore, solubility of contaminants for the beads or granules is solubility of the contaminants at a concentration of not more than 1%, and usually not more than 0.1 or 0.2% (since the polymer is usually made up as a concentration not in excess of around 2 or 5% by weight).

A preferred reverse phase polymerisation process according to the invention comprises providing a dispersion of aqueous monomer phase droplets in a continuous phase in which is dissolved polymeric stabiliser for stabilising the droplets, and polymerising the monomer in the droplets to produce a dispersion of aqueous polymer droplets in the continuous phase, and this process is characterised in that the stabiliser is dissolved in the continuous phase and is a polymer containing ionisable groups whereby the substantially unionised polymer is hydrophobic and soluble in the continuous phase and substantially water insoluble, and the ionised polymer is soluble in water, the continuous phase is a volatile liquid which is partially water miscible and is wholly miscible with water at a concentration of 0.1%, and the aqueous monomer phase contains water soluble ethylenically unsaturated monomer or monomer blend and water and includes a component which is salt forming with the ionisable stabiliser whereby the stabiliser concentrates at the interface of the aqueous and continuous phases and acts as a surfactant.

This process can be used to produce an emulsion of the aqueous polymer droplets (having a size at least 90% below 10 $\mu$m) in the continuous phase, but preferably the process is followed by a drying process to recover the dry polymer particles from the continuous phase either as beads (when the aqueous monomer droplets are bead-size) or as granules when the aqueous polymer droplets are emulsion particles below 10 $\mu$m, preferably below 3 $\mu$m, in size. The drying is preferably by spray drying the emulsion of aqueous polymer droplets, thereby forming the granules.

The granules of the invention are agglomerates of primary particles which are substantially spherical. This substantially spherical shape arises because the primary particles are formed essentially as droplets in a liquid phase. Some fracturing and distortion of the droplets may occur, but the shape will always be much more spherical than is obtainable by, for instance, comminuting preformed particles.

The primary particles have a size at least 90% by weight below 10 $\mu$m, and usually at least 99% by weight below 10 $\mu$m. Generally they are at least 90% by weight below 5 $\mu$m. Usually at least 90% by weight are between 0.1 and 5 $\mu$m, most usually between 0.2 and 1 $\mu$m.

The granules have a size at least 90% by weight above 10 $\mu$m and often above 20 $\mu$m. Typically at least 50% by weight are above 50 $\mu$m. Generally at least 90% by weight are below 500 $\mu$m.

The primary particles can be formed of linear polymer, in which event the aqueous monomer phase is free of cross linking agent. However the invention is of particular value when the primary particles are below 10 $\mu$m and the polymer is branched or cross linked as a result of cross linking the polymer during polymerisation or subsequently. Generally therefore the preferred primary particles are emulsion polymer particles made by polymerisation of water soluble ethylenically unsaturated monomer or monomer blend in the presence of a cross linking agent which is usually a polyethylenically unsaturated crosslinking agent which is included in the blend. Examples are methylene bisacrylamide, tetra allyl ammonium chloride and pentaerythritol triacrylate. Other systems for crosslinking can be used instead of or in addition to this. For instance covalent crosslinking through pendant groups can be achieved, for instance by the use of ethylenically unsaturated epoxy or silane monomers, or by the use of polyfunctional crosslinking agents such as silanes, epoxies, polyvalent metal compounds or other known crosslinking systems.

The amount of crosslinker (if present) and the polymerisation conditions (for instance the initiator system) are selected in conventional manner so as to obtain particles having the desired properties. The primary particles may be polymer of low molecular weight, eg up to IV 1 or 2 dl/g, but the polymerisation is preferably conducted under conditions that favour the production of a high molecular weight polymer.

For instance the initiator and other polymerisation conditions are preferably such that in the absence of the crosslinker, the polymerisation leads to a polymer having IV of at least 4 dl/g and preferably at least 6 dl/g, for instance up to 10 or 15 dl/g or higher, when the polymer is cationic, and values of above this, for instance 10 to 30 dl/g, when the polymer is anionic or nonionic. IV is intrinsic viscosity measured by a suspended level viscometer at 25° C. in 1N sodium chloride buffered to pH 7.

If, as is often preferred, cross linker is present, the actual IV values will be lower because of the cross linking caused by the cross linker.

When the cross linking is conducted in order to provide a polymer having a viscosifying effect, the amount of crosslinker is generally at least 10 ppm and usually at least 50 ppm and more usually above 100 or 200 ppm. Often amounts of 2000 ppm are sufficient but in some instances amounts of up to 5000 ppm, 10000 ppm or more are suitable.

When the cross linking is to render the particles branched or slightly cross linked (for instance as described in EP-A-202,780) the amount of cross linker is generally from 5 to 200, often 5 to 50 or 100 ppm. These amounts are the amounts used when the cross linking is by a polyethylenically unsaturated cross linking agent. Equivalent amounts of other cross linking systems can be derived in known manner. Ionic Regain values (as defined in EP 202,780) typically are 15 to 70%, preferably 25 to 60%, when the polymer is cationic.

The water soluble ethylenically unsaturated monomer or monomer blend can be formed from any of the monomers known to be suitable for the intended use of the polymer. These monomers can be nonionic, anionic or cationic or they can be an anionic blend or a cationic blend or an amphoteric blend.

Suitable non-ionic monomers include acrylamide and vinyl pyrrolidone. Suitable anionic monomers include the salts of ethylenically unsaturated carboxylic or sulphonic acids, for instance sodium acrylate or acrylamide methyl sulphonic acid sodium salt. Suitable cationic monomers include quaternary salts of dialkylaminoalkyl(meth)-acrylates and -acrylamides and diallyldimethyl ammonium chloride.

The preferred polymer particles are homopolymers of dialkylaminoalkyl(meth) acrylate (usually as quaternary salt) or copolymers with other ethylenically unsaturated monomer such as acrylamide and its derivatives. For cosmetic and other viscosifiers, the amount of the cationic monomer is usually at least 50%, for instance 60 to 100%. For other viscosifiers and for flocculants and other purposes any conventional cationic monomer can be used and the amount can be less, for instance down to 20 to 30% by weight or sometimes even down to 3% by weight of the monomers.

Other polymer particles that can be made in the invention are anionic for instance sodium polyacrylate, or nonionic polymers for instance polyacrylamide.

Conventional reverse phase polymerisation is conducted in a hydrophobic liquid which is immiscible in water, but this has the disadvantage that any residual traces of the liquid would impart opacity to the aqueous gel, even if only very small quantities of the solvent were trapped in the granules. Accordingly, in the invention, the continuous phase of the dispersion is a partially water-miscible liquid, by which we mean it is a liquid which has sufficiently low miscibility with water that the aqueous monomer can be dispersed in it without substantial dissolution of water or monomer, but does have sufficient water miscibility that any trace amounts which are trapped in the granules are at a level below the limit of solubility of the liquid in water. For instance the amount of liquid trapped in the granules which provide a 1% gel (or even a 5% gel) will always be below 0.1% by weight based on the gel and so a liquid which has a solubility of at least 1% in water will always tend to give a clear gel.

The partially water miscible liquid must be volatile in order that it is relatively easily stripped out of the granules during the spray drying. Accordingly its boiling point should generally be below 200° C., preferably below 150° C. and more preferably below 100° C. Preferred partially water miscible liquids are esters, such as ethyl acetate or butyl acetate. Other esters which can be used include methyl acetate and butyl propionate or other alkyl alkanoates, generally containing not more than 12 carbon atoms. Other liquids which can be used include ketones and alcohols. Blends with minor, non-interfering, amounts of other liquids such as iso-paraffins or paraffins can be used.

The stabilising system consists of the materials necessary to hold the aqueous monomer dispersed in the volatile liquid. Non-polymeric surfactants, such as sorbitan oleates, are traditionally used in emulsions for this purpose, in quite large amounts (eg 3–15% by weight of polymer). However many of the non-polymeric surfactants which might be suitable tend to be immiscible with and/or insoluble in water, as well as being relatively non-volatile, with the result that they cannot be used in products which are to give a clear gel. Also, the use of the volatile liquid in the continuous phase necessitates the use of surfactants having low HLB, and this again indicates that the surfactants will tend to be insoluble in water and will tend to give an opaque gel, especially in the relatively large amounts of surfactant that are often required as stabiliser. Also, the presence of conventional surfactants in the typical amounts is undesirable in many personal care gels and other aqueous compositions formed from the dried polymer. Preferably the granules and the polymerising compositions contain below 0.5% or 1% or 2% (based on dry weight of polymer) of such surfactants, and preferably the granules and the polymerising compositions are free of them.

The amphipathic polymeric stabilisers which are traditionally used for stabilising reverse phase dispersions are soluble in oil and insoluble in water, and they are non-volatile, so that they will remain in the granules, with the result that dissolution of the granules in water will give an opaque gel or other heterogeneous product. In the invention, however, we use as stabiliser a stabiliser which contains ionisable groups whereby the substantially unionised polymer is hydrophobic and soluble in the continuous phase and substantially water insoluble, by which we mean that the stabiliser will partition preferentially into the continuous phase rather than going into the aqueous phase. In order that the stabiliser is soluble in the continuous phase which is only partially water miscible, the polymer must be hydrophobic when unionised and thus the polymer must include hydrophobic groups.

The stabiliser polymer can be a copolymer of non-ionisable hydrophobic monomer groups and ionisable monomer groups or it can be a polymer of ionisable monomer groups which are hydrophobic when unionised and relatively hydrophilic when ionised together with other monomer groups which can be hydrophilic or hydrophobic.

As a result of including sufficient of the ionisable groups, the ionised polymer can be soluble in water at the pH and concentration conditions typically prevailing during the use of the composition, so that the stabiliser goes into solution and does not interfere with the appearance or performance of the polymer in the aqueous solution.

The stabiliser has to concentrate at the interface between the aqueous monomer phase and the continuous phase and so the monomer phase should include a component which is salt-forming with the ionisable stabiliser whereby the stabiliser will concentrate at the interface due to the preferential solubility of the ionised groups at the interface in the aqueous phase, and the stabiliser will then act as a surfactant. This makes it unnecessary to use any of the conventional non-polymeric surfactants.

In general the aqueous monomer phase should have a pH such as to cause sufficient (but relatively low) ionisation such that the stabiliser concentrates at the interface as a stabiliser, and the pH of the gel should be such that the stabiliser ionises sufficiently (and often completely or almost completely, eg more than 70%) that it gives a clear solution.

When, as is preferred, the polymer particles are cationic, the stabilising polymer is preferably a polymer of amine monomer groups. The amine monomer groups are usually both derived from ethylenically unsaturated amines, for instance dialkylaminoalkyl(meth) acrylates. A small proportion of these amino groups may be in the form of quaternary amino groups, so as to provide sufficient, but not too much, ionisation for the polymer to be effective as stabiliser during the polymerisation (i.e. without relying on the pH of the aqueous monomer phase), but generally the ionisation is by the formation of an acid addition salt, merely by the exposure of the monomer groups to sufficiently acidic conditions from the aqueous monomer phase.

For instance the stabiliser may be initially formed from monomer groups which include non-ionised, free amine, monomer groups and the aqueous monomer phase may include a controlled amount of an acid to give the required degree of ionisation and thus the required solubility and partitioning properties of the stabiliser for it to concentrate at the interface and act as a surfactant.

Accordingly, when the primary polymer particles are cationic, one preferred way of making them is by copolymerising the monomer blend in the presence of a stabiliser containing free amino monomer groups (e.g., a copolymer of ionisable monomer with other hydrophobic monomer) and an appropriate amount of an added acid. This acid can be citric acid but can be any water soluble (including partially water soluble) acid that can cause the desired ionisation at the interface.

When the polymer is anionic, the stabiliser may be a polymer containing carboxylic acid groups (normally a copolymer of hydrophobic monomer groups, free carboxylic acid monomer groups) and appropriate amount of added alkali. When the polymer is non-ionic, the stabiliser may be either cationic or anionic in nature.

The stabiliser can be a copolymer of non-ionisable hydrophobic monomer groups, with ionisable monomer groups. Suitable non-ionisable monomer groups are selected from alkyl(meth) acrylates or styrenes. Examples are compounds in which the alkyl groups are $C_{1-8}$ alkyl, for instance ethyl (or fatty alkyl) for instance $C_{12-24}$ alkyl such as stearyl. Others are vinyl acetate, VeoVa (vinyl ester of versatic acid), n-alkyl acrylamides and non-ionised dialkylamino alkyl (meth) acrylates and acrylamides.

The weight ratio of hydrophobic monomer groups to ionisable monomer groups is generally in the range 10:90 to 90:10, in particular 30:70 to 70:30, even 40:60 to 60:40.

The ratio must be such that when the groups are ionised in the gel the amount of stabiliser carried into the gel by the granules will be such that the stabiliser is fully dissolved in water to give a clear solution at the chosen pH of the gel. For instance, when the ionisable groups are amino groups, a clear solution is generally obtained when the gel has a pH ranging from, for instance, as low as 2 or 3, up to about pH 7, with most monomer blends. However when larger amounts of the amino groups are present it is possible to obtain a clear gel with amino stabilisers and cationic primary polymer at pH values as high as 8.

Other polymeric stabilisers which can be used in the invention are polymers of ionisable groups which are hydrophobic when unionised together with hydrophilic groups. The ionisable hydrophobic groups can be, for instance, dialkylaminoalkyl (meth) acrylates. The comonomer can then be hydrophilic, for instance a polyethylene glycol ester of methacrylic acid or acrylic acid.

In general the polymer which forms the stabiliser is soluble in an aqueous composition (such as a gel) formed from the viscosifier or flocculant and preferably also soluble in deionised water, at a pH of from about 2 to about 10. In particular it is soluble at a pH of from about 3 to about 7. Stabilisers which are particularly useful are soluble in gel or deionised water at pH from 3 to 6.5, especially pH 4.5 to 6. Thus preferably the ionisable groups are ionisable at these pH's, in particular the groups are such that at least 70% of them are ionised at that pH.

In order to promote the formation of a stable, polymerisable dispersion despite the use of a continuous phase which is slightly miscible with water, it is preferred to minimise the amount of water in the aqueous monomer phase and so preferably the amount of water in the monomer phase is in the range 5 to 70%, usually 10 to 40%, or 10 to 30%, by weight of the monomer phase. The monomer or monomer blend must be substantially immiscible with the volatile liquid.

In order to minimise problems that might then arise from exothermic polymerisation, it is preferred for the amount of the monomer phase to be relatively low compared to the amount of continuous phase. Thus the final dispersion typically contains 50 to 75%, often around 55 to 70%, by weight of the continuous phase and 10 to 40%, often around 20 to 35%, dry weight of monomer or polymer, together with the stabiliser which is generally present in an amount of 3 to 25% by weight of the dispersion or 2 to 15% by dry weight of the monomer or polymer.

The polymerisable aqueous phase preferably has an electrolyte concentration (due to ionic monomer, and the resultant ionic polymer, and/or added acid or alkali or other electrolyte) in order to promote the phase separation between the aqueous phase and the continuous phase. Thus, by keeping the amount of water in the aqueous phase relatively low, and especially when using ionised or ionisable monomers optionally with added electrolyte, this will tend to reduce the tendency for water to migrate into the continuous phase or for the continuous phase to migrate into the aqueous phase.

The spray drying can be conducted under conventional spray drying conditions using a conventional spray drier, and the granule size can be controlled in known manner by appropriate selection of spray drying orifices, rate of pumping through the orifices and rate of drying (temperature and drier dimensions) of the spray dried material. The granules have a size at least 90% by weight above 10 $\mu$m, preferable above 20 $\mu$m, typically at least 90% above 50 $\mu$m, and generally below 500 $\mu$m. Preferred size ranges are 100 to 200 $\mu$m. The granules may be used in the form in which they are manufactured by spray drying, but if desired they may be agglomerated into agglomerates of granules.

The total amount of contaminants in the granules will usually be as low as possible and so will always be below 30% and preferably below 20% by dry weight of the granules, and generally it is below 15% by dry weight of the granules. It cannot be reduced to zero because of the residual polymeric stabiliser and other residual contamination and so is usually at least 2 or 3%. Often it is in the range 5 to 10%. Most or all of this is usually the copolymer. Thus the contaminants usually consist wholly or mainly of the copolymer in an amount typically of 2 to 15%, for instance 3 or 5% up to 10% based on the dry weight of the granules, together with trace amount of the volatile liquid and other residues of the polymerisation. These trace amounts often amount to not more than 1% or at the most 2% by weight of the granules.

The granules may also contain, in addition to the primary particles and the contaminants, low levels of water. For instance, they may contain up to 10% (based on dry weight of the granules) water, for instance about 3 or 5 to 7% water.

The preferred compositions are linear or cross linked viscosifiers which will provide clear gels.

By requiring a clear gel we mean that the clarity, measured by a Hach DR/2000 spectrophotometer compared to water, is less than 25 NTU and is preferably less than 10 NTU.

The preferred compositions of the invention exhibit good clarity throughout the pH range 3 to 6.5 and sometimes higher (eg to pH 8), especially around 4.5 to 6, and thus the preferred polymers are particularly suitable for the formulation of clear gels that are compatible with the skin. The amount of polymer in the gel can be very low, if the gel is intended instead merely to be a viscous fluid, but is usually at least 0.5% and preferably at least 1%, in order to give a relatively stiff gel. In some instances it may be up to 2% or even 5%. Naturally it is preferred that the granules should not only give a clear gel at the 1% concentration defined above, but also at whatever concentration is used in practice.

The gels containing cross-linked polymer may be used as thickeners, rheology modifiers, film forming or suspending agents in cosmetic, household, pharmaceutical, and other personal care compositions. Gels comprising cationic polymers will be substantive to skin, hair and some textiles, and therefore the gels may find application as conditioning agents or softening agents in cosmetic, personal care, household, or textile treatment compositions.

Other products according to the invention are useful as flocculants in pollution control and water industries and as retention aids in the paper industry, and as general industrial viscosifiers.

The following are examples

EXAMPLE 1

A stabiliser was formed by feeding 50 g ethyl acrylate, 50 g dimethyl aminoethyl methacrylate and 40 g of a 2% solution of Vazo 67 in ethyl acetate into a vessel containing 60 g refluxing ethyl acetate and 0.2 g Vazo 67 over 3 hours. The contents were then held for a further 1 hour at reflux before being cooled. This resulted in a 50% active copolymer of ethyl acrylate and dimethyl aminoethyl methacrylate.

EXAMPLE 2

An aqueous monomer was formed containing 36.6 g water, 1 g citric acid, 0.2 g methylenebisacrylamide and 100 g dimethyl aminoethyl methacrylate quaternised with methyl chloride. A continuous phase was formed of 200 g ethyl acetate and 20 g of the stabiliser prepared in Example 1.

The aqueous monomer phase was dispersed into the oil phase with homogenisation in a conventional manner, degassed with nitrogen, then initiated with a continuous feed of a 0.1% aqueous solution of sodium metabisulphite and 0.1% tertiary butylhydroperoxide at a rate of 0.1 ml/minute at a starting temperature of 10° C. until polymerisation was complete at 40° C.

In the absence of methylenebisacrylamide, the IV of the polymer would have been about 6.

The resultant dispersion of aqueous polymer particles in ethyl acetate had an average particle size of 450 nm.

This dispersion was then subjected to spray drying at a temperature of 180° C. to provide granules having an average particle size of 20 µm.

When 1% by weight of these granules were mixed with 99% water, and formulated at pH 5.5, the resultant product was a gel having a clarity below 25 NTU.

EXAMPLE 3

An aqueous monomer phase was formed containing 40 g acrylic acid, 36.2 g of 46% sodium hydroxide solution, 0.03 g methylenebisacrylamide and 73.8 g water. A continuous phase was formed of 500 g ethyl acetate and 20 g of a stabiliser of composition butyl acrylate/methacrylic acid (90/10 by weight), prepared in a similar manner to Example 1.

The aqueous phase was dispersed into the oil phase with homogenisation by a conventional manner, degassed with nitrogen, then initiated in a similar manner as Example 2.

This dispersion was then subjected to spray drying at a temperature of 180° C. to provide granules having a particle size of 25 µm.

When 1% by weight of these granules were mixed with 99% water, and formulated at pH 7, the resultant product was a gel having a clarity below 25 NTU.

EXAMPLE 4

An aqueous monomer was formed containing 41.6 g water, 0.7 g citric acid and 100 g dimethyl amino ethyl acrylate quaternised with methyl chloride. A continuous phase was formed of 151.2 g ethyl acetate and 10 g of stabiliser of composition 45:45:10, methoxy PEG 350 methacrylate:dimethyl amino ethyl methacrylate:lauryl methacrylate prepared in similar manner to example 1.

The aqueous monomer phase was dispersed into the oil phase with homogenisation in a conventional manner, degassed with nitrogen, then initiated in similar manner to example 2.

The resulting dispersion of aqueous polymer particles in ethyl acetate was then subjected to spray drying at 180° C. The resulting powdered polymer had an IV of 8.8. After dissolution in water, the polymer was found to behave as a flocculant in a pollution control application for municipal waste treatment, i.e., sewage sludge flocculation.

What is claimed is:

1. A particulate product comprising polymer particles which are substantially spherical and have been made by reverse phase polymerisation of water soluble ethylenically unsaturated monomer or monomer blend and which are contaminated by 2 to 30% by weight non-aqueous contaminants wherein the contaminants are water miscible and include at least 2% by weight stabiliser polymer which contains ionisable groups whereby the stabiliser is soluble in water when substantially ionised but substantially insoluble in water when substantially non-ionised and the contaminants are substantially free of materials which are not soluble in water at the pH at which the ionisable groups are substantially ionised.

2. A product according to claim 1 in which the contaminants consist substantially only of the stabiliser polymer and 0 to 2% volatile liquid, and wherein the volatile liquid is wholly miscible with water at a concentration of 0.1% and the water soluble ethylenically unsaturated monomer or monomer blend is immiscible with the volatile liquid.

3. A product according to claim 1 in which the polymer particles are of cationic polymer and the ionisable groups are provided by ethylenically unsaturated monomer which contains amino groups.

4. A product according to claim 1 in which the polymer particles are formed of 50 to 100 weight % dialkylaminoalkyl(meth)-acrylate or -actylamide or a quaternary or acid addition salt thereof, together with 0 to 50% other ethylenically unsaturated comonomer.

5. A product according to claim 1 in which the polymer particles are a substantial homopolymer of dimethylaminoethyl methacrylate or dimethylamino acrylate, as quaternary ammonium or acid addition salt.

6. A product according to claim 1 in which the polymer particles have been made in the presence of cross linking agent.

7. A product according to claim 1 in the form of spray dried granules which have a size at least 90% by weight above 10 µm and which are formed of primary polymer particles and a minor amount of contaminants, wherein the primary particles are substantially spherical particles having a size at least 90% by weight below 10 µm and formed from a polymer of water soluble ethylenically unsaturated monomer or monomer blend, and the contaminants are present in an amount of 2 to 30% by weight, based on dry weight of the granules and include at least 2% by weight, based on dry weight of the granules, of the ionisable stabiliser.

8. A product according to claim 7 in which the granules provide a gel having a clarity of less than 25 NTU when mixed with deionised water to provide a composition containing 1% by weight of the granules and having a pH at which the ionisable groups are ionised.

9. A clear gel having a clarity of less than 25 NTU and which is an aqueous composition obtained by mixing granules according to claim 8 with water at a pH at which the stabiliser copolymer is substantially completely ionised.

10. A gel according to claim 9 in which the polymer is cationic and the pH is from 3 to 6.5.

11. A household or cosmetic, pharmaceutical or other personal care composition comprising a gel according to claim 9.

12. A method of using a product according to claim 7 as a flocculant or viscosifier in which the primary particles are crosslinked to provide clear gels throughout the pH range of 3 to 6.5, which comprises adding at least 0.5% of the product to an aqueous phase.

13. A reverse phase polymerisation process comprising providing a dispersion of aqueous monomer phase droplets in a continuous phase in which is dissolved a polymeric stabiliser for stabilising the droplets and polymerising the monomer in the droplets to produce a dispersion of aqueous polymer droplets in the continuous phase, characterised in that the stabiliser is dissolved in the continuous phase and is a polymer containing ionisable groups whereby the substantially unionised polymer is hydrophobic and soluble in the continuous phase and substantially water insoluble, and the ionised polymer is soluble in water, the continuous phase is a volatile liquid which is partially water miscible and is wholly miscible with water at a concentration of 0.1% in water at 25° C., and the aqueous monomer phase contains water soluble ethylenically unsaturated monomer or monomer blend and water and includes a component which is salt forming with the ionisable stabiliser whereby the stabiliser concentrates at the interface of the aqueous and continuous phases and acts as a surfactant.

14. A process according to claim 13 in which the stabiliser contains ionisable amine groups, the monomer or monomer blend is cationic, and the monomer phase comprises water soluble acid for ionising the stabiliser.

15. A process according to claim 13 in which the amount of water in the monomer phase is 10 to 40% by weight of the monomer phase, the amount of continuous phase is 50 to 75% by weight of the dispersion and the amount of stabiliser is 2 to 15% by weight based on the dry weight of monomer.

16. A process according to claim 1 in which the stabiliser is a copolymer of non-ionisable hydrophobic monomer groups and ionisable monomer groups.

17. A process according to claim 1 in which the volatile solvent is an alkyl alkanoate containing not more than 12 carbon atoms.

18. A process according to claim 13 in which the aqueous polymer droplets have a size of at least 90% below 10 µm and the process comprises the additional step of drying the dispersion and thereby forming granules having a size at least 90% by weight above 10 µm.

19. A process according to claim 18 in which the drying is by spray drying.

20. A process according to claim 17 in which the volatile solvent is ethyl or butyl acetate.

* * * * *

UNITED STATES PATENT AND TRADEMARK OFFICE
CERTIFICATE OF CORRECTION

PATENT NO. : 6,407,161 B1  
APPLICATION NO. : 09/508149  
DATED : June 18, 2002  
INVENTOR(S) : Howard Roger Dungworth Page 1 of 1

It is certified that error appears in the above-identified patent and that said Letters Patent is hereby corrected as shown below:

On Title page,
    Item (73) Assignee should read:

Item -- (73) Ciba Specialty Chemicals Water Treatment Limited
          Bradford, West Yorkshire, Great Britain --.

Signed and Sealed this

Third Day of March, 2009

JOHN DOLL  
*Acting Director of the United States Patent and Trademark Office*